(12) United States Patent
Hautvast et al.

(10) Patent No.: US 10,888,381 B2
(45) Date of Patent: Jan. 12, 2021

(54) REGISTRATION APPARATUS FOR INTERVENTIONAL PROCEDURE

(71) Applicant: KONINKLIJKE PHILIPS N.V., Eindhoven (NL)

(72) Inventors: Guillaume Leopold Theodoros Frederik Hautvast, Veldhoven (NL); Dirk Binnekamp, Borne (NL); Shyam Bharat, Arlington, MA (US); Ehsan Dehghan Marvast, New York, NY (US); Jochen Kruecker, Washington, DC (US); Molly Lara Flexman, Melrose, MA (US); Amir Mohammad Tahmasebi Maraghoosh, Melrose, MA (US)

(73) Assignee: Koninklijke Philips N.V., Eindhoven (NL)

( * ) Notice: Subject to any disclaimer, the term of this patent is extended or adjusted under 35 U.S.C. 154(b) by 750 days.

(21) Appl. No.: 15/119,151

(22) PCT Filed: Jan. 28, 2015

(86) PCT No.: PCT/EP2015/051646
§ 371 (c)(1),
(2) Date: Aug. 16, 2016

(87) PCT Pub. No.: WO2015/128145
PCT Pub. Date: Sep. 3, 2015

(65) Prior Publication Data
US 2017/0014191 A1 Jan. 19, 2017

Related U.S. Application Data

(60) Provisional application No. 62/067,566, filed on Oct. 23, 2014.

(30) Foreign Application Priority Data

Feb. 27, 2014 (EP) .................................... 14156922

(51) Int. Cl.
*A61B 34/20* (2016.01)
*A61B 17/34* (2006.01)
(Continued)

(52) U.S. Cl.
CPC .............. *A61B 34/20* (2016.02); *A61B 5/066* (2013.01); *A61B 8/0841* (2013.01);
(Continued)

(58) Field of Classification Search
CPC .. A61N 1/30; A61N 2005/1012; A61B 34/20; A61B 17/3403; A61B 10/0241; A61B 2034/2061; A61B 2090/061
See application file for complete search history.

(56) References Cited

U.S. PATENT DOCUMENTS 6,129,670 A * 10/2000 Burdette .................. A61B 8/42
600/427
8,718,349 B2 5/2014 Florent et al.
(Continued)

FOREIGN PATENT DOCUMENTS

CN 203274953 U 11/2013
EP 1142606 A2 10/2001
(Continued)

OTHER PUBLICATIONS

Francis T.S. Yu, et al., (Editor), "Fiber Optic Sensors", 2002, CRC Press, ISBN-13: 9780824707323.

*Primary Examiner* — Bill Thomson
*Assistant Examiner* — Aminah Asghar (57) ABSTRACT

A registration apparatus registers an elongated introduction element (18), like a catheter or a needle, during an inter-
(Continued)

ventional procedure, for instance, a brachytherapy or a biopsy. A guide element (13) includes at least one opening which guides the introduction element when being introduced into a living being (2) through the opening. A temperature profile generation element (14) associated with the opening generates a characteristic temperature profile at the opening for being transferred to the introduction element when being present in the opening. A temperature determination unit (15) determines a temperature along the introduction element, and a registration unit (16) registers the introduction element. The registering includes identifying the transferred characteristic temperature profile on the introduction element based on the determined temperature. This allows the registration unit to register the introduction element during the introduction process in a simple and efficient manner.

20 Claims, 9 Drawing Sheets

(51) Int. Cl.
| | | |
|---|---|---|
| *A61B 90/00* | (2016.01) | |
| *A61B 5/06* | (2006.01) | |
| *A61B 17/00* | (2006.01) | |
| *A61N 5/10* | (2006.01) | |
| *A61B 8/08* | (2006.01) | |
| *A61B 10/02* | (2006.01) | |

(52) U.S. Cl.
CPC ...... *A61B 10/0241* (2013.01); *A61B 17/3403* (2013.01); *A61B 90/37* (2016.02); *A61N 5/1007* (2013.01); *A61N 5/1049* (2013.01); *A61B 2017/00084* (2013.01); *A61B 2017/00477* (2013.01); *A61B 2017/3407* (2013.01); *A61B 2017/3411* (2013.01); *A61B 2017/3413* (2013.01); *A61B 2034/2055* (2016.02); *A61B 2034/2061* (2016.02); *A61B 2090/035* (2016.02); *A61B 2090/061* (2016.02); *A61B 2090/0805* (2016.02); *A61B 2090/0811* (2016.02); *A61B 2090/378* (2016.02); *A61N 2005/1012* (2013.01)

(56) References Cited

U.S. PATENT DOCUMENTS

| | | |
|---|---|---|
| 9,439,735 B2 | 9/2016 | Guttman et al. |
| 2007/0043291 A1* | 2/2007 | Fidel .................. A61B 8/12 600/439 |
| 2007/0203552 A1* | 8/2007 | Machold ............... A61M 25/10 607/104 |
| 2008/0249467 A1* | 10/2008 | Burnett .................. A61B 1/313 604/117 |
| 2010/0323411 A1 | 12/2010 | Kawasaki-Shi |
| 2012/0197097 A1* | 8/2012 | Chan .................. A61B 1/00165 600/342 |
| 2012/0327392 A1* | 12/2012 | Schlesinger .......... A61B 5/065 356/32 |
| 2013/0085380 A1 | 4/2013 | Velusamy |
| 2013/0090563 A1 | 4/2013 | Weber |
| 2013/0102891 A1* | 4/2013 | Binnekamp .......... A61N 5/1007 600/424 |
| 2013/0204072 A1* | 8/2013 | Verard .................. A61B 8/483 600/8 |
| 2014/0105245 A1 | 4/2014 | Forster |
| 2014/0155965 A1* | 6/2014 | Kulstad .................... A61F 7/12 607/105 |
| 2014/0194757 A1* | 7/2014 | 'T Hooft .............. A61B 5/0261 600/505 |

FOREIGN PATENT DOCUMENTS

| | | | | |
|---|---|---|---|---|
| WO | WO-2012101555 A1 * | 8/2012 | ............ | G01B 11/18 |
| WO | 2013030749 A2 | 3/2013 | | |
| WO | 2013090528 A1 | 6/2013 | | |
| WO | 2014049521 A1 | 4/2014 | | |

* cited by examiner

REGISTRATION APPARATUS FOR INTERVENTIONAL PROCEDURE

CROSS-REFERENCE TO PRIOR APPLICATIONS

This application is the U.S. National Phase application under 35 U.S.C. § 371 of International Application Serial No. PCT/EP2015/051646, filed on Jan. 28, 2015, which claims the benefit of United States Application Serial No. 62/067,566, filed on Oct. 23, 2014 and European Patent Application No. 14156922.8, filed Feb. 27, 2014. These applications are hereby incorporated by reference herein.

FIELD OF THE INVENTION

The present invention relates to a registration apparatus, a registration method and a registration computer program for registering an elongated introduction element, like a catheter or a needle, during an interventional procedure, for instance, a brachytherapy or a biopsy. The present invention relates further to a system for performing an interventional procedure comprising the registration apparatus. Yet further, the present invention relates to an imaging system for imaging an elongated introduction element within a living being during an interventional procedure comprising the registration apparatus.

BACKGROUND OF THE INVENTION

In low-dose rate (LDR) brachytherapy and high-dose rate (HDR) brachytherapy an elongated introduction element, like a catheter or a needle, for introducing a radiation source is introduced into a person by a physician under ultrasound imaging guidance, in order to treat an inner region of the person with radiation emitted by the radiation source. The introduction element is typically introduced into the person through an opening of a guide element, like a grid template, and has to be visualized during the introduction procedure in the image coordinate frame of the ultrasound probe. Since the identification of the introduction element directly in the ultrasound image is difficult and often inaccurate, technologies have been developed for determining the shape of the introduction element, such as optical shape sensing (OSS). With these technologies, however, the registration of the introduction element during the introduction process has still been a challenge so far.

SUMMARY OF THE INVENTION

It is an object of the present invention to provide a registration apparatus, a registration method and a registration computer program for registering an elongated introduction element during an interventional procedure, which allows registering the introduction element in a simple and efficient manner.

In a first aspect of the present invention, a registration apparatus for registering an elongated introduction element is presented, the introduction element being adapted to be introduced into a living being for performing an interventional procedure within the living being, wherein the registration apparatus comprises:

a guide element comprising at least one opening for guiding the introduction element when being introduced into the living being through the opening, a temperature profile generation element associated with the opening for generating a characteristic temperature profile at the opening for being transferred to the introduction element when being present in the opening, a temperature determination unit for determining a temperature along the introduction element, and a registration unit for registering the introduction element, wherein the registering comprises identifying the transferred characteristic temperature profile on the introduction element based on the determined temperature.

Since the temperature profile generation element associated with the opening generates a characteristic temperature profile at the opening for being transferred to the introduction element when being present in the opening and since the temperature determination unit determines a temperature along the introduction element, by identifying the transferred characteristic temperature profile on the introduction element based on the determined temperature, the registration unit can register the introduction element during the introduction process in a simple and efficient manner.

The characteristic temperature profile that is generated at the opening is preferably a temperature profile that is different from, for instance, the temperature of the environment in which the registration apparatus is used, such that, when the introduction element is present in the opening, the transferred characteristic temperature profile can reliably be identified on the introduction element based on the temperature determined along the introduction element.

It is preferred that the registration unit is adapted to identify the position of the transferred characteristic temperature profile on the introduction element and to register the location of the introduction element based on the identified position.

For instance, in an embodiment, the introduction element has a tip and an elongated body for being introduced into the living being through the opening, wherein the registration unit is adapted to register the location of the tip of the introduction element relative to the opening. In particular, the opening is preferably adapted to guide the introduction element into a particular direction, here, referred to as the z-axis direction, wherein the registration unit is adapted to register the location of the tip of the introduction element relative to the opening. This may be performed by vectorially adding a linear distance between the identified position of the transferred characteristic temperature profile on the introduction element and the tip to a known location of the opening. Of course, the location of the tip may also be registered relative to another reference point that has a known spatial relationship to the opening. For instance, the location of the tip may be registered with respect to a specific point of the guide element.

Preferably, the temperature profile generation element is arranged within the opening. This can lead to a very compact and robust design of the guide element.

It is preferred that the introduction element comprises one or more optical shape sensing fibers for optical shape sensing, wherein the temperature determination unit is adapted to sense the temperature along the introduction element based on strains induced by the temperature in the optical shape sensing fibers.

If the introduction element comprises optical shape sensing fibers, the registration unit is preferably adapted to register the location of the introduction element further using optical shape sensing. This allows for an accurate registration even if the introduction element is not straight, but curved for example, because the introduction element bends when it comes into contact with a tissue, an organ, or the like within the living being. In one example, the entire length of the introduction element may be equipped with the optical shape sensing fibers, such that the location of the entire length including the tip of the introduction element can be registered relative to the opening at any time during the introduction process.

In general, fiber optic sensing involves integrating optical fibers into instruments to determine strain, temperature, voltage, shape, etc. Typically, the determination process involves processing the reflected light that is received after emitting light into the optical fibers, which are equipped with fiber optic sensors. In the present invention, strain is preferably determined using fiber bragg gratings, which reflect a particular part of the incoming light spectrum as a function of strain. By combining optical fibers with multiple fiber bragg gratings, it is possible to measure the temperature-induced strain as well as to integrate the strains from, for instance, three or more optical fibers along the instrument to reconstruct the shape thereof in real-time (so-called optical shape sensing). For more details regarding the determination of temperature and shape using fiber optic sensing, reference is made, for instance, to Francis T. S. Yu and Shizhuo Yin (Editors), "Fiber Optic Sensors", 2002, Dekker Inc., which is herewith incorporated by reference.

Thus, in the present invention, by making use of an introduction element that comprises optical shape sensing fibers, the temperature determination functionality and, for instance, a registration functionality for registering the entire length including the tip of the introduction element, can be implemented by means of the same technology.

In an embodiment, the at least one opening comprises a plurality of the openings, wherein each opening comprises a presence identification element for identifying the presence of the introduction element in the opening and for providing an opening identification information identifying the opening, wherein the registration unit is adapted to register the introduction element based on the opening identification information.

During some interventional procedures, such as a low dose rate (LDR) brachytherapy or a prostate biopsy, the introduction element has to be introduced into the living being to a plurality of closely spaced locations. Such interventional procedures may efficiently be performed by using a guide element which comprises a plurality of openings.

The guide element is preferably a grid template, in which the openings are arranged in a two-dimensional grid, preferably, a regular grid. In such a grid template, the openings are preferably adapted to guide the introduction element into a direction which is perpendicular to the plane of the grid template, here, referred to as the x-y-plane. By registering the introduction element based on the opening identification information identifying the opening in which the introduction element is present, the registration unit can, when registering the location of the introduction element, easily account for the location of the introduction element in the x-y-plane. Of course, also when the direction into which the openings guide the introduction element is not perpendicular to the plane of the grid template, or when different openings are adapted to guide the introduction element into different directions, or when the openings are not arranged in a two-dimensional grid, in particular, a regular grid, the opening identification information can be of help for registering the location of the introduction element, provided that the spatial relationships between the openings and the reference point relative to which the location of the introduction element shall be registered are known.

In addition or in an alternative to registering the location of the introduction element based on the opening identification information, this information may be notified to the physician using a suitable notification mechanism, such as a visible or audible notification.

Preferably, the temperature profile generation element is adapted to generate the characteristic temperature profile at the opening only when it has been identified that the introduction element is present in the opening. This makes it possible to prevent or at least reduce a drift in the temperature of the opening or even the entire guide element over time, which, when using, for instance, optical shape sensing, could lead to a spatial broadening or drift of the strains induced by the temperature in the optical shape sensing fibers and, in turn, to a loss of spatial resolution.

It is preferred that the registration apparatus comprises an opening utilization identification unit for identifying for each opening whether the opening has already been utilized during the interventional procedure, wherein the identifying is based on the opening identification information.

This can serve as a quality check for ensuring that the same opening is not re-utilized during the interventional procedure. For instance, in a typical brachytherapy, such as an LDR brachytherapy, the same opening is not used more than once to deliver a therapy. By identifying whether the opening has already been utilized during the interventional procedure, the physician may be notified when attempting to re-utilize the opening using a suitable notification mechanism, such as a visible or audible notification, and/or the opening may be blocked in some way, such as by means of a mechanical shutter, to prevent a re-utilization of the opening. Preferably, it is identified that the opening has already been utilized if the presence of the introduction element in the opening was already identified earlier for at least a predetermined period of time.

It is further preferred that the presence identification element comprises at least one light source for emitting light and at least one light detector for detecting the light, wherein, when the introduction element is present in the opening, a light path from the light source to the light detector is blocked, wherein the presence identification element is adapted to identify the presence of the introduction element in the opening based on the blocking of the light path.

By using the concept of a "light barrier", the presence of the introduction element in the opening can easily and reliably be identified. Preferably, the presence identification element, in particular, the light source and the light detector, are arranged within the opening. This can lead to a very compact and robust design of the guide element. Moreover, by arranging the presence identification element within the opining, the identification mechanism may be prevented in a more reliable way from generating false reports. Additionally, the light detector may better be shielded from the influence of ambient light, which could decrease the sensitivity thereof.

In an embodiment, the at least one opening comprises a plurality of openings, wherein for each opening, the temperature profile generation element associated with the opening is adapted to generate a different characteristic temperature profile at the opening, wherein the registration apparatus further comprises a presence identification unit for identifying the presence of the introduction element in the opening and for providing an opening identification information identifying the opening, wherein the identification is based on the differences between the characteristic temperature profiles at the openings, wherein the registration unit is adapted to register the introduction element based on the opening identification information.

In this case, a specific presence identification element is not provided for each opening. Rather, for each opening, the presence of the introduction element in the opening is identified based on the differences between the characteristic temperature profiles at the openings. For instance, the characteristic temperature profiles at the openings can be different in their absolute temperatures, or they can be temporally or spatially modulated in different ways, or a combination of these techniques can be used for generating distinct characteristic temperature profiles that can be distinguished from each other.

Also in this embodiment, the guide element is preferably a grid template, in which the openings are arranged in a two-dimensional grid, preferably, a regular grid, and the openings are preferably adapted to guide the introduction element into a direction that is perpendicular to the plane of the grid template, here, referred to as the x-y-plane. By registering the introduction element based on the opening identification information identifying the opening in which the introduction element is present, the registration unit can, when registering the location of the introduction element, easily account for the location of the introduction element in the x-y-plane.

In addition or in an alternative to registering the location of the introduction element based on the opening identification information, this information may be notified to the physician using a suitable notification mechanism, such as a visible or audible notification. Thus, in this case, the registering of the introduction element comprises registering the opening in which the introduction element is present.

Moreover, it can be foreseen that a several introduction elements are simultaneously introduced into the living being through the openings. In this case, the temperature determination unit is preferably adapted to determine a temperature along each of the introduction elements, wherein, since the different characteristic temperature profiles are generated at the openings, the registration unit can preferably be adapted to identify which introduction element is present in which opening. This information may also be notified to the physician using a suitable notification mechanism, such as a visible or audible notification.

It is further preferred that also in this embodiment, the registration apparatus comprises an opening utilization identification unit for identifying whether the opening has already been used during the interventional procedure, wherein the identifying is based on the opening identification information. Preferably, it is identified that the opening has already been utilized if the presence of the introduction element in the opening was already identified earlier for at least a predetermined period of time. It is preferred that the temperature profile generation element comprises at least one light source for generating the characteristic temperature profile by heating with the light source, or that the temperature profile generation element comprises a specific heating and/or cooling element for generating the characteristic temperature profile by heating and/or cooling.

The first variant is particular advantageous if presence identification elements using the concept of a "light barrier", as described above, are provided in the registration apparatus, since in this case the light source can be re-used for also generating the characteristic temperature profile by heating with the light source, resulting in an efficient realization of the registration apparatus. On the other hand, by providing a specific heating and/or cooling element for generating the characteristic temperature profile by heating and/or cooling, the characteristic temperature profile may be generated with a higher accuracy compared to a heating with a light source.

It is preferred that the opening extends along a longitudinal axis and the characteristic temperature profile comprises a spatial temperature gradient in the direction of the longitudinal axis.

Such a spatial temperature gradient in the direction of the longitudinal axis of the opening can be easily and reliably identified. Moreover, compared to, for instance, a temporal temperature gradient, the identification of a spatial temperature gradient can be quicker.

It is further preferred that the temperature profile generation element comprises a heating element and a cooling element for generating the spatial temperature profile by a combination of heating and cooling.

By generating the spatial temperature profile by a combination of heating and cooling, a drift in the temperature of the opening or even the entire guide element over time, which, when using, for instance, optical shape sensing, could lead to a spatial broadening or drift of the strains induced by the temperature in the optical shape sensing fiber and, in turn, to a loss of spatial resolution, can be prevented or at least reduced. The combination of the heating element and the cooling element may consist of two junctions of a thermoelectric element, such as a Peltier element, or the opening may be thermally coupled to such two junctions. Preferably, the heating element and the cooling element are arranged in a spatial proximity, for instance, they can be arranged next to each other in the direction of the longitudinal axis of the opening in order to generate a spatial temperature gradient in this direction.

In a further aspect of the present invention, a system for performing an interventional procedure within a living being is presented, wherein the system comprises:

an elongated introduction element being adapted to be introduced into the living being for performing the interventional procedure within the living being, and a registration apparatus for registering the introduction element as defined in claim 1.

It is preferred that the registration apparatus further comprises a rotation constraining element associated with the opening, wherein the rotation constraining element comprises a first element and the introduction element comprises a second element, wherein the first element and the second element together are adapted to constrain the rotation of the introduction element to a predetermined angle, wherein the registration unit is adapted to register the location of the introduction element based on the predetermined angle.

This is particularly advantageous if the introduction element is curved, because when the rotation of the introduction element is known to be constrained to the predetermined angle, the orientation of its curvature can easily be identified and used for the registration of the location of the introduction element.

In a further aspect of the invention, an imaging system for imaging an elongated introduction element within a living being is presented, the introduction element being adapted to be introduced into the living being for performing an interventional procedure within the living being, wherein the imaging system comprises:

a registration apparatus for registering the introduction element as defined in claim 2, an imaging unit for generating an image showing an inner part of the living being, which includes the registered location of the introduction element, based on the registered location, and a display for displaying the image.

In a further aspect of the present invention, a registration method for registering an elongated introduction element is presented, the introduction element being adapted to be introduced into a living being for performing an interventional procedure within the living being, wherein the registration method comprises:

guiding the introduction element, by using a guide element comprising at least one opening, when being introduced into the living being through the opening, generating a characteristic temperature profile at the opening, by using a temperature profile generation element associated with the opening, for being transferred to the introduction element when being present in the opening, determining a temperature along the introduction element, by using a temperature determination unit, and registering the introduction element, by using a registration unit, wherein the registering comprises identifying the transferred characteristic temperature profile on the introduction element based on the determined temperature.

In a further aspect of the present invention, a registration computer program for registering an elongated introduction element is presented, the introduction element being adapted to be introduced into a living being for performing an interventional procedure within the living being, wherein the registration computer program comprises program code means for causing the registration apparatus as defined in claim 1 to carry out the steps of the registration method as defined in claim 14, wherein the registration computer program is run on a computer controlling the registration apparatus.

It shall be understood that the registration apparatus of claim 1, the system of claim 11, the imaging system of claim 13, the registration method of claim 14, and the registration computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
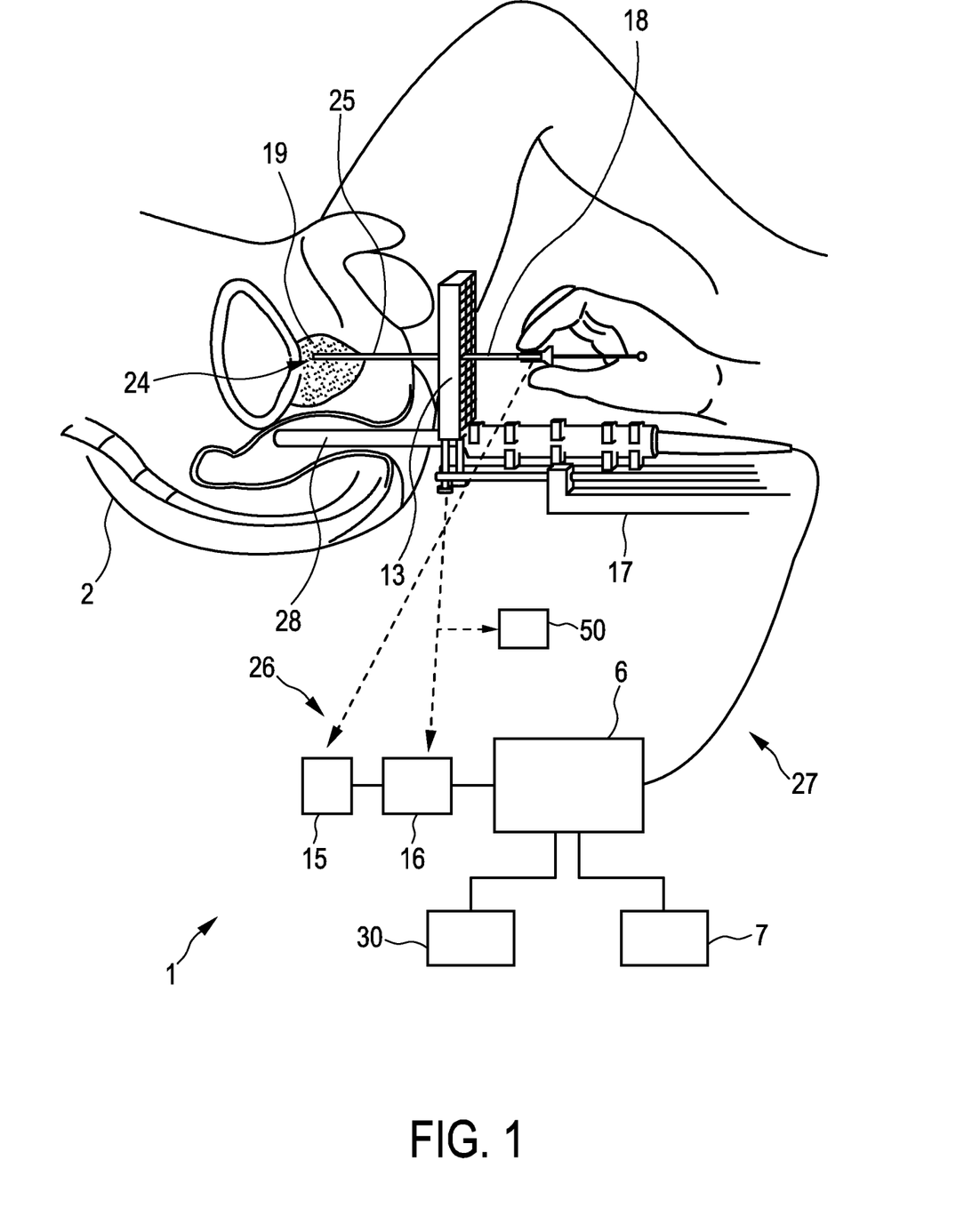
FIG. 1 shows schematically and exemplarily an embodiment of a system for performing a brachytherapy within a person.

FIG. 1 shows schematically and exemplarily an embodiment of a system for performing an interventional procedure, here, a brachytherapy, within a living being 2, which, in this example, is a person. The system 1 comprises an elongated introduction element 18 for introducing a radiation source into the person 2. In this embodiment, the introduction element 18 is a needle, which is introduced into the prostate 19 of the person 2. During the introduction process, an imaging system 27 is used for imaging the introduction element 18 within the person 2.

The imaging system 27 comprises a registration apparatus 26 for registering the introduction element 18, an imaging unit 6, 28 for generating an image showing an inner part of the person 2, which includes the registered location of the introduction element 18, based on the registered location, and a display 7 for displaying the image.

The introduction element 18 is manually inserted into the person 2, in particular, into the prostate 19, under image guidance. In particular, the imaging system 27 is adapted to image the introduction element 18 during an introduction process for performing an LDR brachytherapy or a HDR brachytherapy, wherein the imaging unit 6, 28 is preferentially adapted to update the generated image in real-time based on the actual registered location of the introduction element 18 and wherein the display 7 is adapted to display the updated image in real-time.

The introduction element 18 has a tip 24 and an elongated body 25 to be introduced into the person 2 through an opening, which is comprised by a guide element 13, for guiding the introduction element 18. The guide element 13, here, is a grid template, in which a plurality of the openings are arranged in a two-dimensional, regular grid. It is schematically and exemplarily shown in more detail in FIG. 2.

Figure 2:
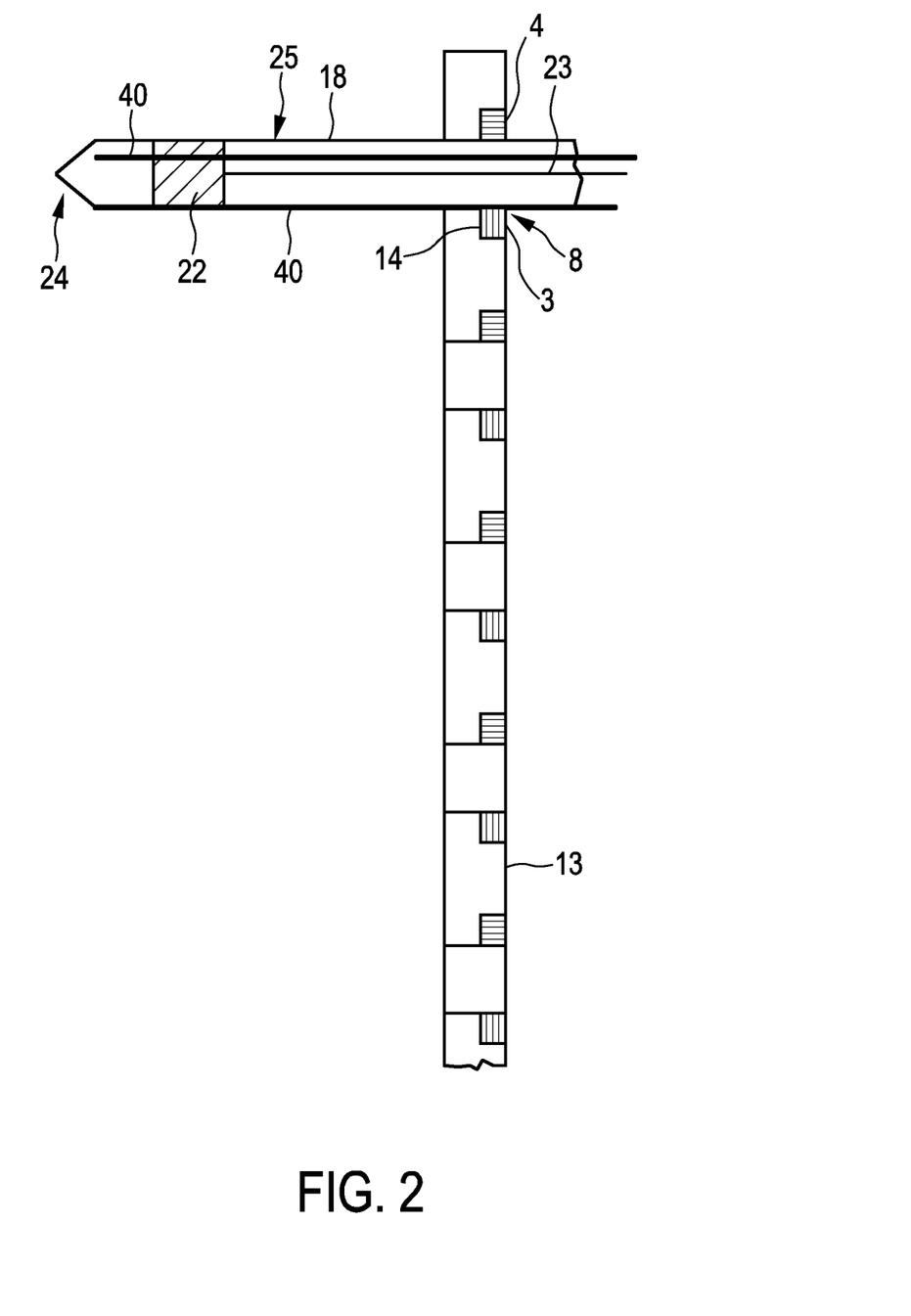
FIG. 2 shows schematically and exemplarily a sectional view of a grid template and an introduction element of the system shown in FIG. 1, FIG. 3 schematically and exemplarily illustrates identifying the presence of the introduction element in an opening of the grid template shown in FIG. 2, FIG. 4 schematically and exemplarily illustrates constraining the rotation of the introduction element.

FIG. 2 is a sectional view showing schematically and exemplarily the grid template 13 with the openings 8, wherein through one of these openings 8, the introduction element 18 is introduced into the person 2. In particular, the openings 8 are adapted to guide the introduction element 18 into a particular direction, here, referred to as the z-axis direction, which is perpendicular to the plane of the grid template 13, here, referred to as the x-y-plane. Within the introduction element 18, the radiation source 22 for emitting radiation to a target region, here, the prostate 19 of the person 2, is located. The radiation source 22, which is preferentially a radioactive radiation source, can be moved within the introduction element 18 by using the connection 23, which may be a wire or another mechanical connection.

The registration apparatus 26 comprises, in addition to the grid template 13, for each opening 8, a temperature profile generation element 14 associated with the opening 8 for generating a characteristic temperature profile at the opening 8. When the introduction element 18 is present in the opening 8, the characteristic temperature profile is transferred to the introduction element 18. Here, the temperature profile generation element 14 comprises at least one light source 3, which is arranged within the opening 8, for generating the characteristic temperature profile by heating with the light source 3.

The registration apparatus 26 further comprises a temperature determination unit 15 for determining a temperature along the introduction element 18, and a registration unit 16 for registering the introduction element 18, wherein the registering comprises identifying the transferred characteristic temperature profile on the introduction element 18 based on the determined temperature.

In this embodiment, the registration unit 16 is adapted to identify the position of the transferred characteristic temperature profile on the introduction element 18 and to register the location of the introduction element 18 based on the identified position.

For instance, the registration unit 16 can be adapted to register the location of the tip 24 of the introduction element 18 relative to the opening 8. This may be performed by vectorially adding a linear distance between the identified position of the transferred characteristic temperature profile on the introduction element 18 and the tip 24 to a known location of the opening 8.

Here, the introduction element 18 comprises one or more, here, three (only two of which are shown in FIG. 2), optical shape sensing fibers 40 for optical shape sensing, wherein the temperature determination unit 15 is adapted to sense the temperature along the introduction element 18 based on strains induced by the temperature in the optical shape sensing fibers 40.

In this embodiment, the registration unit 16 is then adapted to register the location of the introduction element 18 using optical shape sensing. This allows for an accurate registration even if the introduction element 18 is not straight, but curved for example, because the introduction element 18 bends when it comes into contact with a tissue, an organ, or the like within the living being. In this example, the entire length of the introduction element 18 is equipped with the optical shape sensing fiber 40, such that the location of the entire length including the tip 24 of the introduction element 18 can be registered relative to the opening 8 at any time during the introduction process.

Here, each opening 8 comprises a presence identification element 3, 4 for identifying the presence of the introduction element 18 in the opening 8 and for providing an opening identification information identifying the opening 8, wherein the registration unit 16 is adapted to register the introduction element 18 based on the opening identification information.

During the brachytherapy, the introduction element 18 has to be introduced into the person 2 to a plurality of closely spaced locations. This is efficiently performed by using the grid template 13, which comprises a plurality of the openings 8. In the grid template 13, the openings 8 are adapted to guide the introduction element 18 into a direction which is perpendicular to the plane of the grid template 13, here, referred to as the x-y-plane. By registering the introduction element 18 based on the opening identification information identifying the opening 8 in which the introduction element 18 is present, the registration unit 16 can, when registering the location of the introduction element 18, easily account for the location of the introduction element 18 in the x-y-plane.

In addition to registering the location of the introduction element 18 based on the opening identification information, this information may be notified to the physician using a suitable notification mechanism, such as a visible or audible notification.

The registration apparatus 26, here, further comprises an opening utilization identification unit 50 for identifying whether the opening 8 has already been used during the brachytherapy, wherein the identifying is based on the opening identification information.

This serves as a quality check for ensuring that the same opening 8 is not re-utilized during the brachytherapy. By identifying whether the opening 8 has already been utilized during the brachytherapy, the physician is notified when attempting to re-utilize the opening 8 using a suitable notification mechanism (not shown in the figures), such as a visible or audible notification. Alternatively, the opening 8 may be blocked in some way (not shown in the figures), such as by means of a mechanical shutter, to prevent a re-utilization of the opening 8. In this embodiment, it is identified that the opening 8 has already been utilized if the presence of the introduction element 18 in the opening 8 was already identified earlier for at least a predetermined period of time.

In this embodiment, the presence identification element 3, 4 comprises at least one light source 3 for emitting light and at least one light detector 4 for detecting the light, wherein, when the introduction element 18 is present in the opening 8, a light path from the light source 3 to the light detector 4 is blocked, wherein the presence identification element 3, 4 is adapted to identify the presence of the introduction element 18 in the opening 8 based on the blocking of the light path. This is shown in more detail in FIG. 3, which schematically and exemplarily illustrates identifying the presence of the introduction element 18 in the opening 8 of the grid template 13.

Figure 3:
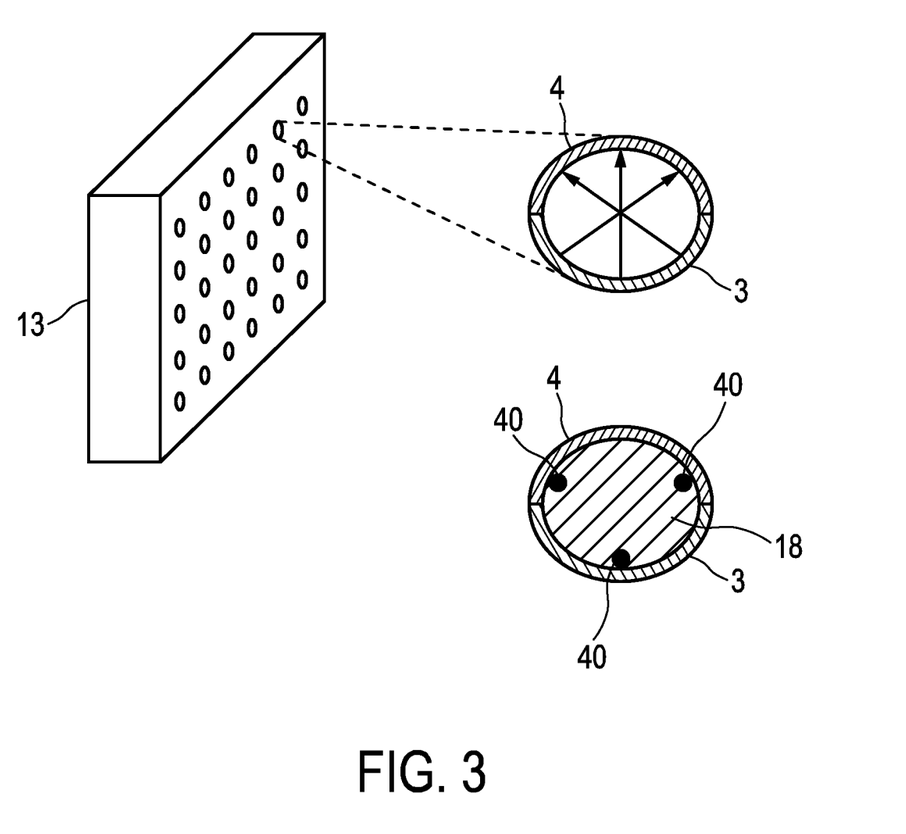

By using the concept of a "light barrier", the presence of the introduction element 18 in the opening 8 can easily and reliably be identified. In this embodiment, the light source 3, which, in this case, is the same light source 3 as utilized for generating the characteristic temperature profile at the opening 8, and the light detector 4 are arranged within the opening 8, which among other advantages leads to a very compact and robust design of the grid template 13.

Figure 4:
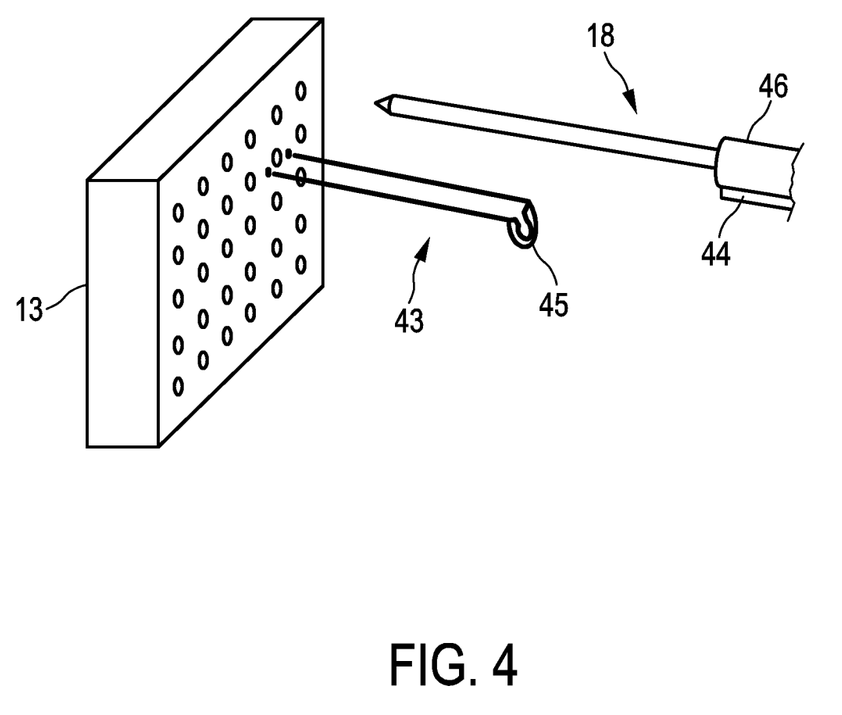

FIG. 4 schematically and exemplarily illustrates constraining the rotation of the introduction element 18. Here, the registration apparatus 26 further comprises a rotation constraining element 43 associated with the opening 8. The rotation constraining element 43 comprises a first element 45, here, a notch or recess, and the introduction element 18 comprises a second element 44, here, a longitudinal protrusion on a handle 46, wherein the first element 45 and the second element 44 together are adapted to constrain the rotation of the introduction element 18 to a predetermined angle, wherein the registration unit 18 is adapted to register the location of the introduction element 18 based on the predetermined angle. In particular, if the introduction element 18 is curved, since the rotation of the introduction element 18 is known to be constrained to the predetermined angle, the orientation of its curvature can easily be identified and used for the registration of the location of the introduction element 18.

Figure 5:
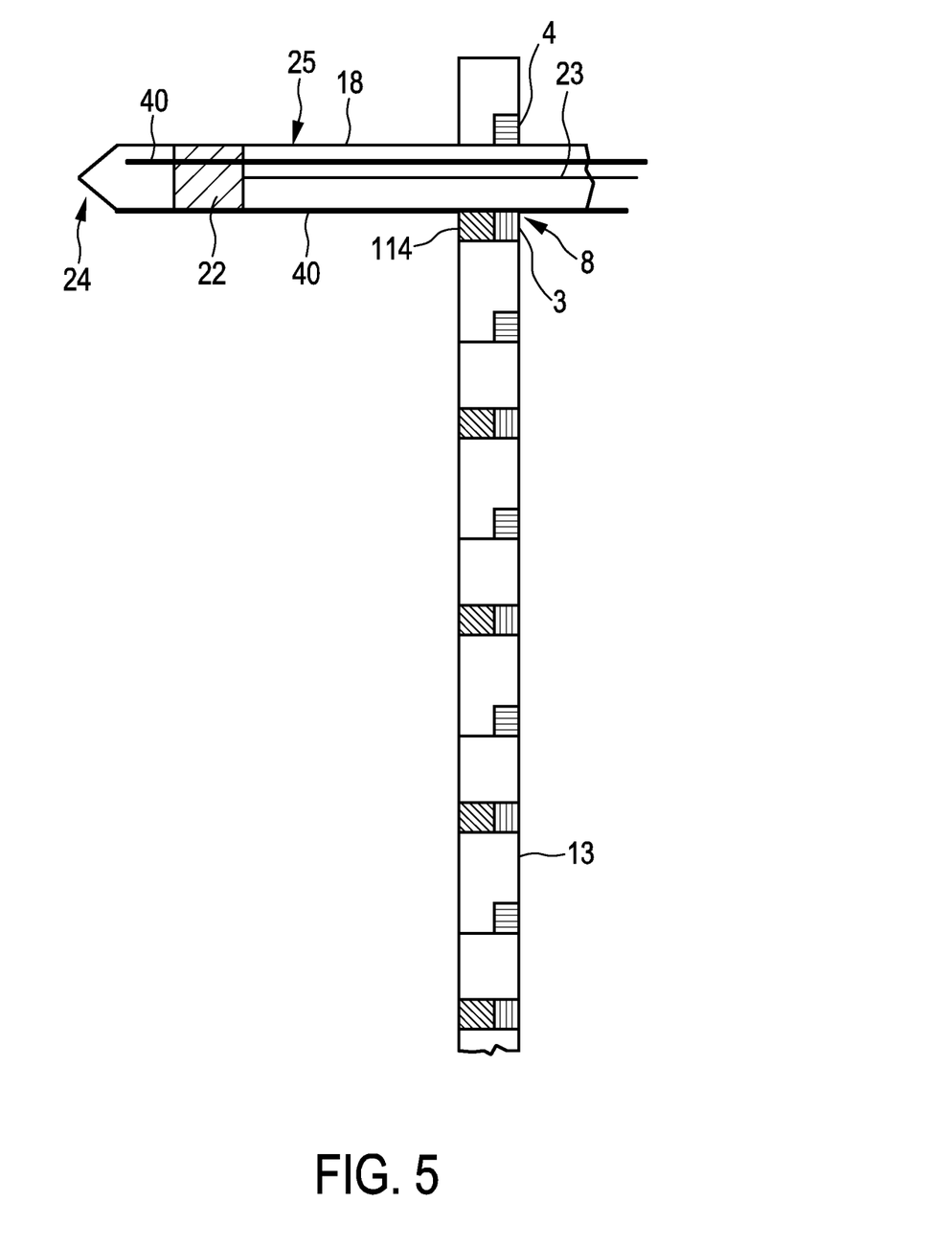
FIG. 5 shows schematically and exemplarily a sectional view of a grid template and an introduction element of a variant of the system shown in FIG. 1.

FIG. 5 shows schematically and exemplarily a sectional view of a grid template 13 and an introduction element 18 of a variant of the system 1 shown in FIG. 1. This variant is similar to the system 1, however, here, the temperature profile generation element 114 comprises a specific heating and/or cooling element for generating the characteristic temperature profile by heating and/or cooling. It is schematically and exemplarily shown in more detail in FIG. 6.

Figure 6:
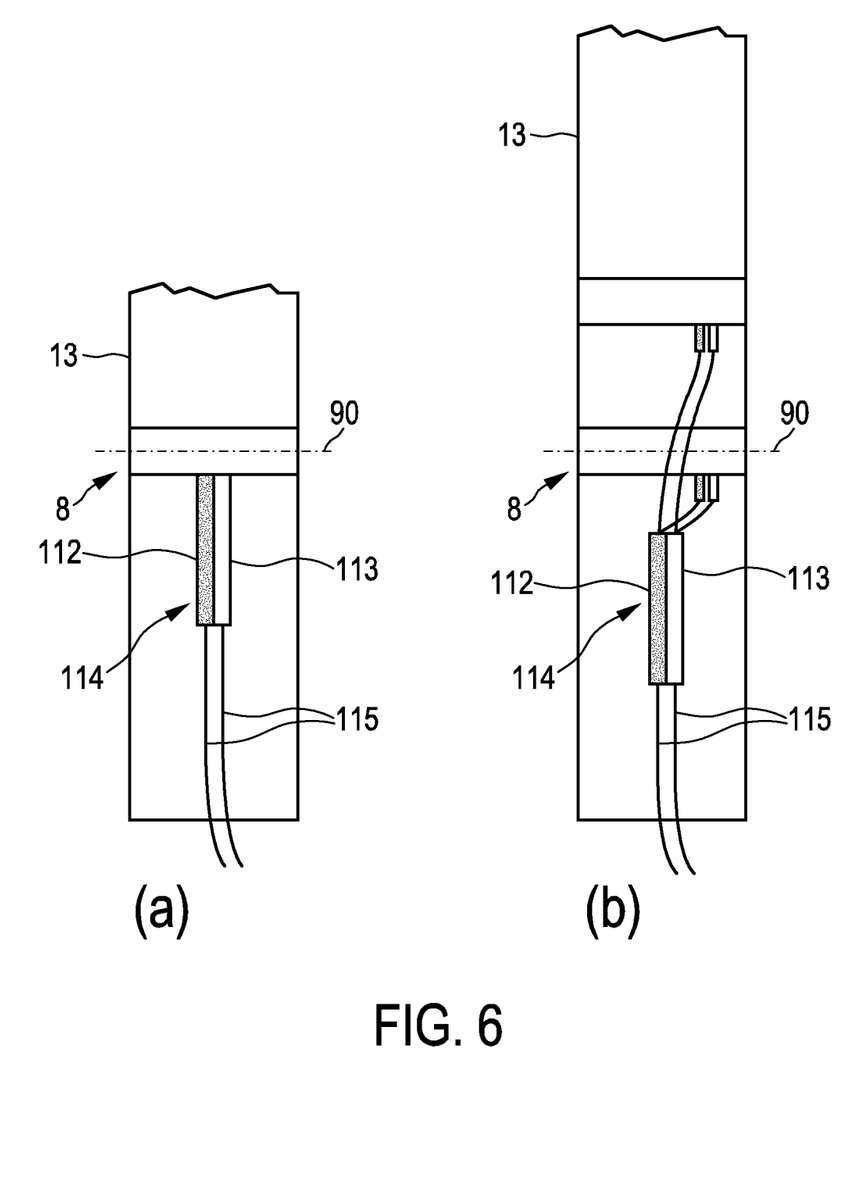
FIG. 6 shows schematically and exemplarily a temperature profile generation element of the variant of the system shown in FIG. 1.

In FIG. 6, the opening 8 is shown to extend along a longitudinal axis 90 and the temperature profile generation element 114 comprises a heating element 113 and a cooling element 112 for generating the spatial temperature profile by a combination of heating and cooling, wherein, in this case, the characteristic temperature profile comprises a spatial temperature gradient in the direction of the longitudinal axis 90.

Such a spatial temperature gradient in the direction of the longitudinal axis 90 of the opening 8 can be easily and reliably identified. Moreover, compared to, for instance, a temporal temperature gradient, the identification of a spatial temperature gradient can be quicker.

Moreover, by generating the spatial temperature profile by a combination of heating and cooling, a drift in the temperature of the opening 8 or even the entire grid template 13 over time, which could lead to a spatial broadening or drift of the strains induced by the temperature in the optical shape sensing fibers 40 and, in turn, to a loss of spatial resolution, can be prevented or at least reduced. The combination of the heating element 113 and the cooling element 112, here, consists of two junctions of a thermoelectric element, in particular, a Peltier element, as illustrated on the left side (a) of the figure. Alternatively, the opening 8 may be thermally coupled to such two junctions, as illustrated on the right side (b) of the figure. In both cases, electrical conductors 115 are provided for powering the thermoelectric element and for controlling the magnitude of the spatial temperature profile. The electrical conductors 115 are connected to a power source (not shown in the figures), which may be integrated into and/or controlled by, for instance, the temperature determining unit 15.

The imaging unit 6, 28 comprises a three-dimensional transrectal ultrasound probe 28 attached to a support element 17, to which also the grid template 13 is attached. The support element 17 ensures that the template grid 13 and the ultrasound probe 28 are fixed during the brachytherapy. Before the brachytherapy, in particular, before the introduction process, the imaging unit 6, 28 and the registration unit 28 have been registered with respect to each other such that a location in an image reference frame can be transformed to a location in a registration reference frame and vice versa. Since the grid template 13 and the ultrasound probe 28 are fixed during the entire brachytherapy, this transformation for transforming locations between the image reference frame and the registration reference frame is valid through the entire brachytherapy. Thus, for instance, the location of each opening 8 of the grid template 13 is known within the image reference frame, that is, especially the location of the opening 8 of the grid template 13 through which the introduction element 18 is introduced into the person 2, is known in the image reference frame. Therefore, after the location of the tip 24 and/or the elongated body 25 of the introduction element 18 has been identified based on the known location of the opening 8 of the grid template 13, through which the introduction element 18 is introduced into the person 2, the location of the tip 24 within the person 2 is also known in the reference imaging frame.

The imaging unit 6, 28 comprises the ultrasound probe 28 and an image generation unit 6. If the registration unit 16 is adapted to register the location of the tip 24 of the introduction element 18, the image generation unit 6 can be adapted to determine a tip slice within the person 2 including the registered location of the tip 24 of the introduction element 18 and to generate a tip image representing the tip slice. The display 7 is adapted to display the generated tip image.

The imaging unit 6, 28 can be adapted to determine an axial tip slice and/or a sagittal tip slice and to generate an axial tip image and/or a sagittal tip image representing the axial tip slice and/or the sagittal tip slice, respectively, wherein the display 7 may be adapted to display the generated axial tip image and/or the sagittal tip image. In an embodiment, the imaging unit 6, 28 can be adapted to determine the tip slice such that it is perpendicular to the elongated body 25 of the introduction element 18.

Here, the registration unit 16 is adapted to identify the location of the elongated body 25, wherein the imaging unit 6, 28 is adapted to determine a body slice within the person 2 including a length of the elongated body 25 and to generate a body image representing the body slice, wherein the display 7 is adapted to display the generated body image. In particular, the imaging unit 6, 28 is adapted to determine the body slice such that the determined body slice includes a maximal portion of the length of the elongated body 25. The imaging unit 6, 28 may further be adapted to determine further body slices including further portions of the length of the elongated body 25 and to generate further body images representing the determined further body slices within the person 2, wherein the display 7 may be adapted to display the further body images. The imaging unit 6, 28 may be adapted to determine an axial tip slice and/or a sagittal body slice and to generate an axial tip image and/or a sagittal body image representing the axial tip slice and/or the sagittal body slice, respectively, wherein the display 7 may be adapted to display the generated axial tip image and/or the sagittal body image.

Thus, the display 7 can display one or several images showing, for instance, the tip 24 and/or the elongated body 25 of the introduction element 18 within the person 2 during the introduction process. For instance, an axial image plane may be chosen to include the registered position of the tip 24 of the introduction element 18 and/or an image plane showing the maximum length of the introduction element 18 may be reconstructed from the ultrasound image volume and displayed on the display 7. Alternatively or in addition, a sagittal image may be adjusted to show the slice that contains the maximum portion or extent of the introduction element 18 and one or several further sagittal images corresponding to the reminder of the introduction element 18 may be presented, for instance, as thumbnail images, wherein the imaging unit may comprise an input unit 30 like a keyboard, a computer mouse, a touchpad, et cetera for allowing a user to select one of these thumbnail images to be displayed larger.

The imaging unit 6, 28 is preferentially adapted to cover a volume of the person 2, which allows the imaging unit 6, 28 to generate desired image slices, without having to physically displace the ultrasound probe 28. If, in an embodiment, the imaging unit 6, 28 does not cover an imaging volume being large enough for generating all desired image slices, the ultrasound probe 28 can be mounted on a moving unit controlled by the image generation unit 6 or another control unit depending on the locations of the desired slices within the person 2, which should be imaged. The moving unit can be, for instance, a motorized stepper that positions the ultrasound probe 28 accordingly. This controlled moving unit can also be used, if instead of the three-dimensional ultrasound probe 28 a two-dimensional ultrasound probe having a one-dimensional array of ultrasound transducers is used, that is, also in this case, the ultrasound probe 28 can be positioned such that a desired slice of the person 2 can be imaged. In order to control the moving unit accordingly, the registered location of the introduction element 18 is used.

If the imaging unit 6, 28 is adapted to cover an imaging volume, that is, if the ultrasound probe 28 comprises a two-dimensional array of ultrasound transducers, the imaging unit 6, 28 can be adapted to use the subset of ultrasound transducers from the transducer array, which can be used for generating an ultrasound image slice showing the introduction element 18, in particular, the tip 24 of the introduction element 18. For this selection, the imaging unit 6, 28 can use the registered location of the introduction element 18.

The above described imaging system can be used to assist in introducing an introduction element to be used for performing an LDR brachytherapy or a HDR brachytherapy. In case of an LDR brachytherapy the introduction element may be a needle, which is inserted to adhere to a pre-plan, wherein through the needle one or several radioactive radiation sources may be introduced into the person, in order to implant the one or several radioactive radiation sources in a target region for, for instance, one or several days. In case of HDR brachytherapy the radioactive radiation sources are preferentially not deposited in the target region, but are placed temporarily at different locations within the introduction element, for instance, for some minutes only, and then removed. If the imaging system is used for performing a HDR brachytherapy, the knowledge about the entire three-dimensional shape and pose of the introduction element obtained during the insertion procedure can be used for determining the positions of the radioactive radiation sources, when they are introduced into the introduction element. Thus, the imaging system can also be used to improve the accuracy of placing radioactive radiation sources during a HDR brachytherapy.

Figure 7:
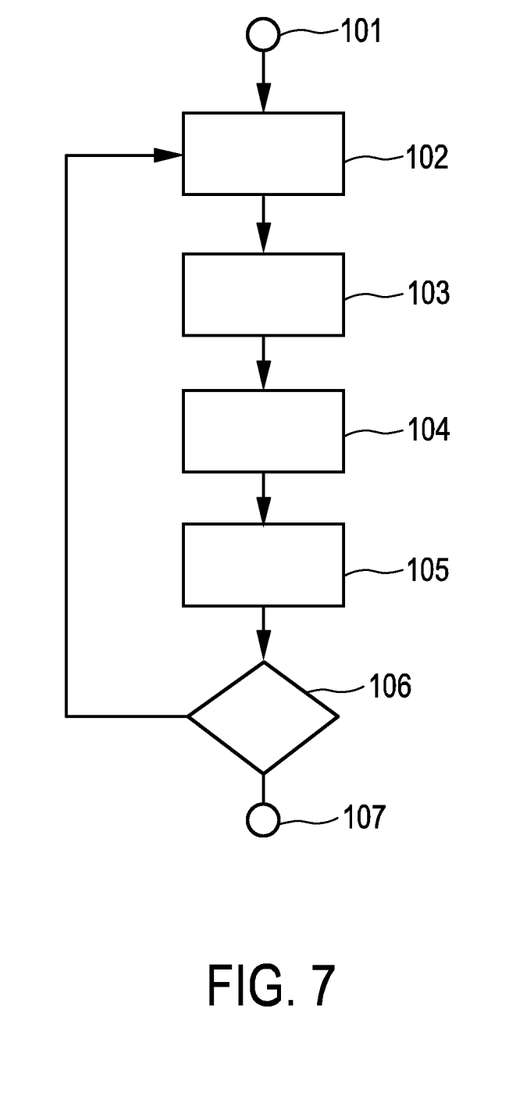
FIG. 7 shows a flowchart exemplarily illustrating an embodiment of a registration method to be used with the system shown in FIG. 1.

In the following an embodiment of a registration method for registering an elongated introduction element 18 will be described with reference to a flowchart shown in FIG. 7, wherein the introduction element 18 is adapted to be introduced into a living being 2, which, in this example, is a person, for performing an interventional procedure, here, a brachytherapy.

In step 101, the system 1 is initialized. In particular, the grid template 13 is arranged adjacent to the person 2 and the ultrasound probe 28 is transrectally introduced into the person 2. In step 102, the introduction element 18 is guided, by using the guide element 13 comprising at least one opening 8, when being introduced into the person 2 through the opening 8. In step 103, a characteristic temperature profile is generated at the opening 8, by using the temperature profile generation element 14, 114 associated with the opening 8, for being transferred to the introduction element 18 when being present in the opening 8. In step 104, a temperature along the introduction element 18 is sensed, by using the temperature determination unit 15. In step 105, the introduction element 18 is registered, by using the registration unit 16, wherein the registering comprises identifying the transferred characteristic temperature profile on the introduction element 18 based on the determined temperature. In step 106, it is determined whether an abort criterion has been fulfilled. If this is the case, the registration method ends in step 107. Otherwise the registration method continues with step 102. Thus, the guiding of the introduction element 18, the generation of the characteristic temperature profile at the opening 8, the sensing of the temperature along the introduction element 18, and the registering of the introduction element 18 are performed in a loop, in order to register in real-time the introduction element 18, until an abort criterion is fulfilled. The abort criterion may be, for instance, whether a user has input via the input 30 that the method should be aborted, whether the tip 24 of the introduction element 18 has reached the target region, whether it is identified that the introduction element 18 is not present any more in the opening 8, et cetera.

Figure 8:
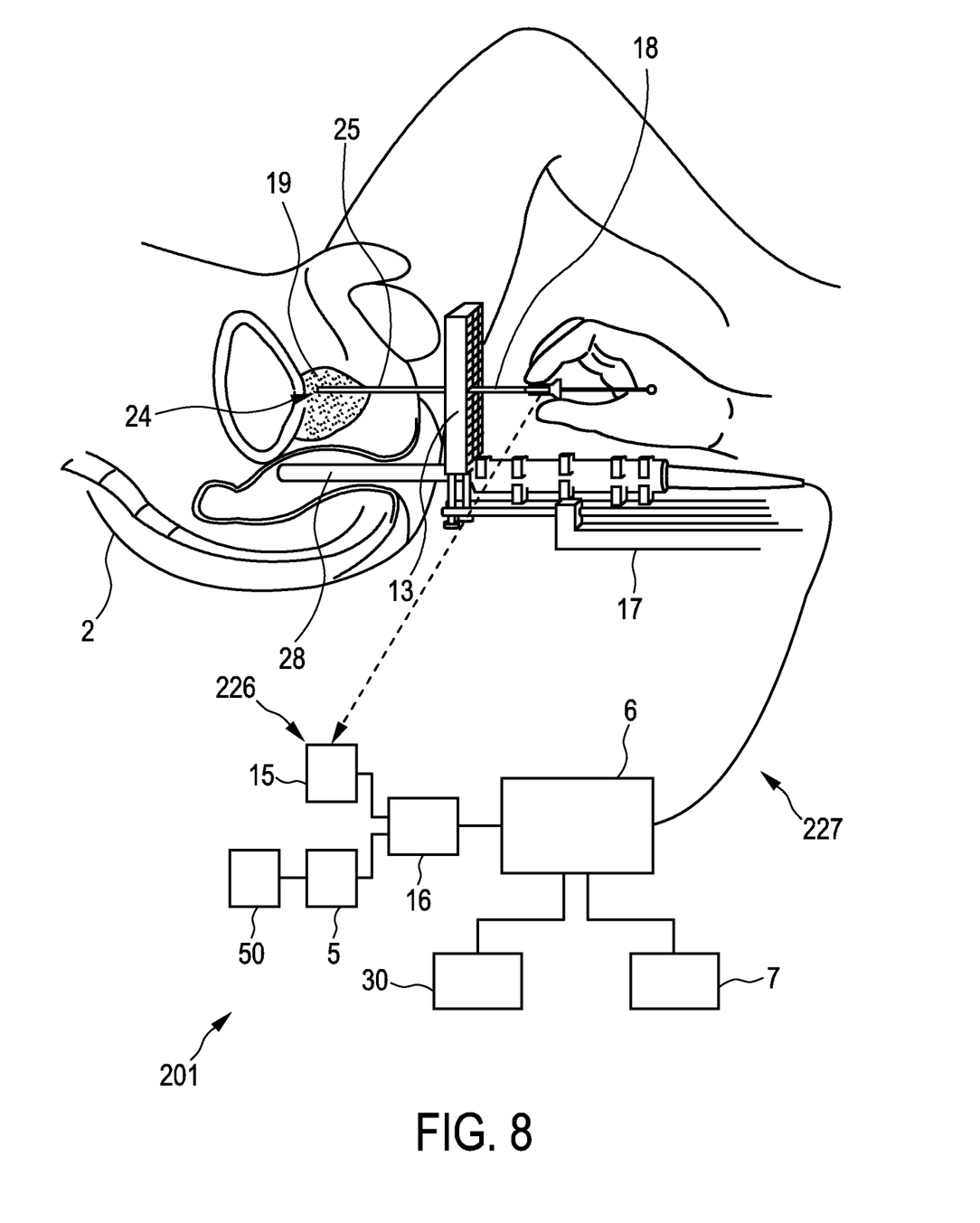
FIG. 8 shows schematically and exemplarily a further embodiment of a system for performing a brachytherapy within a person.
Figure 9:
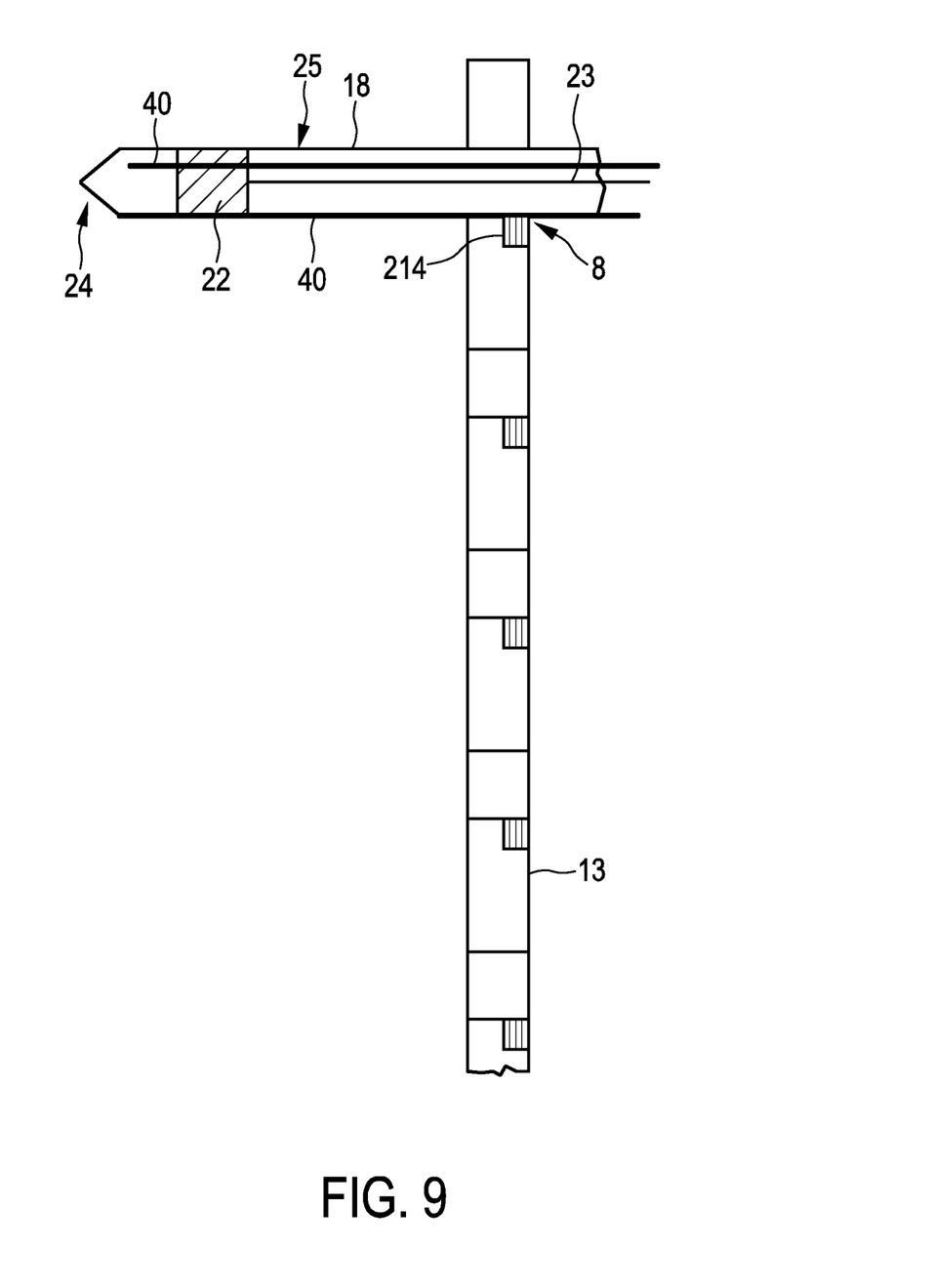
FIG. 9 shows schematically and exemplarily a sectional view of a grid template and an introduction element of the system shown in FIG. 8.

FIG. 8 shows schematically and exemplarily a further embodiment of a system 201 for performing a brachytherapy within a person 2, which is similar to the system 1 described above with reference to FIG. 1. However, in this embodiment, a specific presence identification element is not provided for each opening 8. Rather, as shown in FIG. 9, for each opening 8, the temperature profile generation element 214 is adapted to generate a different characteristic temperature profile, here, comprising a spatial temperature gradient in the direction of the longitudinal axis, at the opening 8. The registration apparatus 226 then further comprises a presence identification unit 5 for identifying the presence of the introduction element 18 in the opening 8 and for providing an opening identification information identifying the opening 8, wherein the identification is based on the differences between the characteristic temperature profiles at the openings 8. As in the system 1, the registration unit 16 is adapted to register the introduction element 18 based on the opening identification information.

Also in this embodiment, the guide element 13 is a grid template, in which the openings 8 are arranged in a two-dimensional, regular grid, and the openings 8 are adapted to guide the introduction element 18 into a direction that is perpendicular to the plane of the grid template, here, referred to as the x-y-plane. By registering the introduction element 18 based on the opening identification information identifying the opening in which the introduction element is present, the registration unit 16 can, when registering the location of the introduction element 18, easily account for the location of the introduction element 18 in the x-y-plane.

In addition or in an alternative to registering the location of the introduction element 18 based on the opening identification information, this information may be notified to the physician using a suitable notification mechanism (not shown in the figures), such as a visible or audible notification. Thus, in this case, the registering of the introduction element 18 comprises registering the opening 8 in which the introduction element 18 is present.

Moreover, it can be foreseen that several introduction elements 18 (only one being shown in the figures) are simultaneously introduced into the person 2 through the openings 8. In this case, the temperature determination unit 15 is adapted to determine a temperature along each of the introduction elements 18, wherein, since the different characteristic temperature profiles are generated at the openings 8, the registration unit 16 can be adapted to identify which introduction element 18 is present in which opening 8. This information may also be notified to the physician using a suitable notification mechanism (not shown in the figures), such as a visible or audible notification.

Also in this embodiment, the registration apparatus 226 comprises an opening utilization identification unit 50 for identifying whether the opening 8 has already been used during the interventional procedure, wherein the identifying is based on the opening identification information. Preferably, it is identified that the opening has already been utilized if the presence of the introduction element in the opening was already identified earlier for at least a predetermined period of time.

Although in above described embodiments the introduction element is adapted to introduce a radiation source into the person for performing a brachytherapy, in other embodiments the introduction element can also be adapted to perform a biopsy. For instance, the introduction element can be a biopsy needle for performing a prostate biopsy procedure.

Although in FIGS. 1 to 5, 8 and 9 only a single introduction element is shown, also several introduction elements can be inserted into the person. Moreover, although in above described embodiments the living being is a person, in other embodiments the living being can also be an animal, and, although in above described embodiments the introduction element is introduced into the prostate, the introduction element may also be inserted into another part of the living being, especially into another organ.

Although in above described embodiments, the temperature generating elements and/or the presence identifying elements are arranged within the openings, in other embodiments, they may also be arranged at the opining, for instance, at a front side or a back side of the grid template.

It shall also be noted that various elements of the registration apparatus may be provided in the form of a retrofit kit for retrofitting an existing guide element, in particular, an existing grid template. For instance, the temperature generating elements, the rotation constraining elements, et cetera may be provided in the form of a retrofit kit for being attached to an existing grid template.

Although the present invention is described herein in the context of an ultrasound imaging system, in other embodiments, the imaging system can also be, for instance, a CT imaging system or an MRI imaging system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of the temperature along the introduction element, the registration of the introduction element, et cetera performed by one or several units or devices can be performed by any other number of units or devices. For instance, the temperature determination unit 15 can be integrated into the registration unit 16 that the registration unit 6 may also determine the temperature along the introduction element. The operations and/or the control of the registration apparatus in accordance with the registration method may be implemented as program code of a computer program and/or as dedicated hardware. The computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A registration apparatus for registering an elongated introduction element, the elongated introduction element being adapted to be introduced into a living being for performing an interventional procedure within the living being, wherein the registration apparatus comprises:
a guide element comprising at least one opening for guiding the elongated introduction element when being introduced into the living being through the opening,
wherein the registration apparatus further comprises:
a temperature profile generation element associated with the opening for generating a characteristic temperature profile at the opening of the guide element, the characteristic temperature profile being transferred to a segment of the elongated introduction element being introduced into the living being and currently located in the opening,
a temperature determination unit for determining a temperature profile along the segment of the elongated introduction element, and
a registration unit for registering the elongated introduction element, wherein the registering comprises identifying the transferred characteristic temperature profile on the segment of the elongated introduction element based on the determined temperature profile.

2. The registration apparatus as defined in claim 1, wherein the registration unit is adapted to identify a position of the transferred characteristic temperature profile on the elongated introduction element and to register the location of the segment of the elongated introduction element based on the identified position.

3. The registration apparatus as defined in claim 1, wherein the elongated introduction element comprises one or more optical shape sensing fibers for optical shape sensing, wherein the temperature determination unit is adapted to sense the temperature along the elongated introduction element based on strains induced by the temperature in the one or more optical shape sensing fibers.

4. The registration apparatus as defined in claim 1, wherein the at least one opening comprises a plurality of the openings, wherein each opening comprises a presence identification element for identifying the presence of the elongated introduction element in the opening and for providing an opening identification information identifying the opening, wherein the registration unit is adapted to register the elongated introduction element based on the opening identification information.

5. The registration apparatus as defined in claim 4, further comprising an opening utilization identification unit for identifying for each opening whether the opening has already been utilized during the interventional procedure, wherein the identifying is based on the opening identification information.

6. The registration apparatus as defined in claim 4, wherein the presence identification element comprises at least one light source for emitting light and at least one light detector for detecting the light, wherein, when the elongated introduction element is present in the opening, a light path from the light source to the light detector is blocked, wherein the presence identification element is adapted to identify the presence of the introduction element in the opening based on the blocking of the light path.

7. The registration apparatus as defined in claim 1, wherein the at least one opening comprises a plurality of openings, wherein for each opening, the temperature profile generation element associated with the opening is adapted to generate a different characteristic temperature profile at each of the plurality of openings, wherein the registration apparatus further comprises a presence identification unit for identifying the presence of the elongated introduction element in each of the plurality of openings and for providing an opening identification information identifying each opening in which the elongated introduction element is present, wherein the identification is based on the differences between the characteristic temperature profiles at the openings, wherein the registration unit is adapted to register the elongated introduction element based on the opening identification information.

8. The registration apparatus as defined in claim 1, wherein the temperature profile generation element comprises at least one light source for generating the characteristic temperature profile by heating with the light source.

9. The registration apparatus as defined in claim 1, wherein the opening extends along a longitudinal axis and the characteristic temperature profile comprises a spatial temperature gradient in the direction of the longitudinal axis.

10. The registration apparatus as defined in claim 9, wherein the temperature profile generation element comprises a heating element and a cooling element for generating the spatial temperature profile gradient by a combination of heating and cooling.

11. The registration apparatus as defined in claim 9, further including:
a rotation constraining element associated with the opening and configured to constrain the rotation of the elongated introduction element.

12. A registration method for using the registration apparatus defined in claim 1, comprising:
guiding the elongated introduction element through the opening of the guide element into the living being through the opening;
generating the characteristic temperature profile at the opening, using the temperature profile generation element associated with the opening;
determining a temperature along a segment of the elongated introduction element located in the opening with the temperature determination unit, and
registering the elongated introduction element with the registration unit, including identifying the characteristic temperature profile transferred to the segment of the elongated introduction element located in the opening.

13. A non-transitory computer-readable medium carrying computer software configured to control the registration apparatus to perform the registration method as defined in claim 12.

14. A registration apparatus for registering an elongated introduction element and a guide plate defining an array of openings configured to receive the elongated introduction element being introduced into a living being through a selected one of openings to perform an interventional procedure within the living being, wherein the registration apparatus comprises:
at least one of a heater and a cooler associated with each opening for generating a characteristic temperature profile in a segment of the elongated introduction element being introduced through the selected one of the openings;
a temperature sensor mounted along the elongated introduction element and configured to sense the characteristic temperature profile associated with the selected one of the openings in the segment of the elongated introduction element; and
a computer processor configured to register the elongated introduction element and the guide plate, wherein the registering includes identifying the transferred characteristic temperature profile sensed by the temperature sensor of the elongated introduction element.

15. The registration apparatus as defined in claim 14, wherein the computer processor is configured to identify a position where the sensed characteristic temperature profile is sensed on the elongated introduction element and to register the position of the sensed characteristic temperature profile along the elongated introduction element.

16. The registration apparatus as defined in claim 14, wherein each opening of the array of openings is associated with a unique characteristic temperature profile, wherein the computer processor further identifies which one of the array of openings of the elongated introduction element is introduced based on the sensed characteristic temperature profile.

17. The registration apparatus as defined in claim 14, wherein the heater associated with each opening includes at least one light source for generating the characteristic temperature profile.

18. The registration apparatus as defined in claim 17, further including:
at least one light detector associated with each opening and configured to receive light from the light source associated with the same opening, such that when the elongated introduction element is present in the opening, a light path from the light source to the light detector is blocked identifying the presence of the elongated introduction element in one of the array of openings based on the blocking of the light path.

19. The registration apparatus as defined in claim 14, wherein each opening of the array of openings extends along a longitudinal axis and the characteristic temperature profile comprises a spatial temperature gradient in a direction of the longitudinal axis.

20. The registration apparatus as defined in claim 19, including both the heater and the cooler offset along the longitudinal axis to generate the spatial temperature profile by a combination of heating and cooling.

* * * * *